United States Patent
Rasmussen et al.

(10) Patent No.: US 7,520,295 B2
(45) Date of Patent: Apr. 21, 2009

(54) CAPILLARY CARRIER WITH LEAK SUPERVISION

(75) Inventors: Per Brandt Rasmussen, Augustenborg (DK); Heiko Arndt, Flensburg (DE)

(73) Assignees: Cequr Aps., Nordborg (DK); Diramo A/S, Nordborg (DK)

( * ) Notice: Subject to any disclaimer, the term of this patent is extended or adjusted under 35 U.S.C. 154(b) by 0 days.

(21) Appl. No.: 10/543,676

(22) PCT Filed: Jan. 24, 2004

(86) PCT No.: PCT/DK2004/000053

§ 371 (c)(1),
(2), (4) Date: Jul. 27, 2005

(87) PCT Pub. No.: WO2004/066802

PCT Pub. Date: Aug. 12, 2004

(65) Prior Publication Data

US 2006/0054230 A1   Mar. 16, 2006

(30) Foreign Application Priority Data

Jan. 28, 2003 (DK) ............................... 2003 00111

(51) Int. Cl.
*F16L 9/18* (2006.01)
*F16L 55/16* (2006.01)

(52) U.S. Cl. .................. 137/312; 73/40.5 R; 165/70; 165/170

(58) Field of Classification Search ............... 137/312; 73/40.5 R; 138/104, 114, 194; 604/113, 604/114, 118, 19, 30, 48, 246; 165/70, 170
See application file for complete search history.

(56) References Cited

U.S. PATENT DOCUMENTS

| 2,838,074 A | * | 6/1958 | Lauck ...................... 285/123.1 |
| 3,485,245 A | * | 12/1969 | Terwilliger et al. ......... 604/114 |
| 4,715,852 A | | 12/1987 | Reinicke et al. ............. 604/131 |
| 4,784,645 A | | 11/1988 | Fischell ...................... 604/153 |
| 5,013,006 A | * | 5/1991 | Furuse .......................... 251/8 |
| 5,288,113 A | * | 2/1994 | Silvis et al. ................. 285/342 |
| 5,360,411 A | | 11/1994 | Mimura et al. ............. 604/153 |
| 5,487,569 A | * | 1/1996 | Silvis et al. .................... 285/24 |

(Continued)

FOREIGN PATENT DOCUMENTS

EP   0 450 186 A1   12/1990

(Continued)

*Primary Examiner*—John Rivell
*Assistant Examiner*—Cloud K Lee
(74) *Attorney, Agent, or Firm*—McCormick, Paulding & Huber LLP

(57) ABSTRACT

In a capillary carrier with an inlet and an outlet, a channel is formed and extends between the inlet and the outlet. At least one capillary tube is arranged within the channel, and sealing elements, by which the capillary tube is sealingly fixed to the channel, are arranged at least near an inlet portion and an outlet portion of the capillary tube. An area is formed limited by a part of the channel, the sealing elements and the exterior of the capillary tube, which is in connection with the exterior of the carrier through a fluid communication pad, whereby a possible fluid leak across the sealing elements will be led to this area, and from there to the exterior of the carrier.

16 Claims, 1 Drawing Sheet

U.S. PATENT DOCUMENTS

| | | | | |
|---|---|---|---|---|
| 5,540,899 A | * | 7/1996 | Koves | 422/200 |
| 5,884,657 A | * | 3/1999 | Srock | 137/312 |
| 6,039,066 A | * | 3/2000 | Selby | 137/312 |
| 6,129,107 A | * | 10/2000 | Jackson | 137/312 |
| 6,142,974 A | * | 11/2000 | Kistner et al. | 604/113 |
| 6,261,261 B1 | * | 7/2001 | Gordon | 604/113 |
| 6,882,797 B2 | * | 4/2005 | Stewart et al. | 392/470 |
| 6,901,216 B2 | * | 5/2005 | Jusiak et al. | 392/470 |

FOREIGN PATENT DOCUMENTS

| | | |
|---|---|---|
| EP | 1 254 676 A1 | 10/1997 |
| FR | 2 577 301 | 8/1986 |
| GB | 1 029233 | 5/1966 |

* cited by examiner

CAPILLARY CARRIER WITH LEAK SUPERVISION

CROSS REFERENCE TO RELATED APPLICATIONS

This application is entitled to the benefit of and incorporates by reference essential subject matter disclosed in International Patent Application No. PCT/DK2004/000053 filed on Jan. 24, 2004 and Danish Patent Application No. PA 2003 00111 filed Jan. 28, 2003.

FIELD OF THE INVENTION

This invention generally relates to a capillary carrier.

BACKGROUND OF THE INVENTION

Capillary carriers of the type employing small capillary tubes that can be placed in a fluid system are known in the art. The capillary carrier provides, besides support for the capillary tube, a fluid interface between the fluid system and the capillary tube. This interface could involve either pipes or hoses, whereby fluid is led from the fluid system to the capillary carrier, and from the capillary carrier back to the fluid system.

The main applications for small capillaries involve the administration of doses of a substance in small quantities. This could be a dosage of medication into a patient, or a dosage of reagent for analysing a liquid sample. Some of these applications, especially those involving the dosage of medication into patients, are very sensitive regarding the dosage amount. Some medications, like insulin for diabetic patients, are deadly if the dosage amount exceeds a given limit, often the lethal amount does not greatly exceed the normal dosage amount.

Regarding the use of insulin, diabetic patients can improve their quality of life and life expectancy by maintaining their blood glucose concentration close to the natural level of a healthy person. However, the amount of insulin required to maintain this level is quite low, and even in a dilution of insulin the dosage amount is rather low. Exceeding the level of insulin in the blood can be life threatening for the patient.

In all known capillary carrier system, there exists the risk of supplying an overdose if a fault situation occurs inside the capillary carrier. This fault situation could be, among other things, a broken capillary tube or a broken seal between capillary tube and capillary carrier.

It is the general object of this invention to provide a safety system within a capillary carrier, by which an increased dosage amount in a fault situation is avoided.

SUMMARY OF THE INVENTION

The object of this invention is achieved by providing a capillary carrier that has an area limited by a part of the channel, the sealing elements and the exterior of the capillary tube, which is in connection with the exterior of the carrier through a fluid communication path, whereby a possible fluid leak across the sealing elements will be led to this area, and from there to the exterior of the carrier.

The carrier is preferably formed from two parts with the channel being defined between the two parts when they are assembled. Each part can be made so that it defines an outer surface structure, with the channel being formed as a cavity inside the carrier due to the interaction of the surface structures.

In an embodiment of the invention the two parts are adhered together in an adhesive. The adhesive also performs as a sealing function between the two parts, and thus prevents fluid from penetrating from the channel into the surface area between the two parts. The sealing between the two parts and between the carrier and the capillary tube is accomplished without the need for any additional elements. The two parts form a single unit without any additional connection means.

In another embodiment of the invention the two parts are held together by a snap-system. A sealing material between the two surfaces facing towards each other prevents fluid from penetrating from the channel into the surface area between the two parts. Accordingly, a mutual engagement force between the two parts is present when the two parts are snapped together. In addition, the two parts will be properly positioned relative to one another. Furthermore, when the sealing material is glue, the force-applying period for curing glue between the two parts can be reduced to zero, as the snap-system will provide the necessary application of force.

It can be preferable that the material forming the carrier has a high heat transfer capability, whereby temperature control of the capillary tube can be accomplished by controlling the exterior surface temperature of the carrier. Accordingly, a dosage amount independent of the surrounding temperature can be obtained, for example by placing the capillary carrier for a medication dosage device directly on a person's skin.

In one embodiment of the invention the carrier forms an upper and a lower section, and each of the capillary tubes has an inlet portion in one of the sections and an outlet portion in the other of the sections. This provides an area inside the capillary carrier between the two sections that will be dry under normal conditions, and only in a fault situation be in connection with the fluid from the fluid system.

In another embodiment of the invention, the inlet and the outlet are both placed in one of the upper or lower section. Thereby, connections between the carrier and fluid system occur in only one section of the carrier.

In still another embodiment of the invention, detection means are in connection with the specified area inside the carrier, allowing fluid leaks across the sealing elements to be detected. This allows for possible fluid leak to be detected while still harmless, but also that it will be detectable and whereby a warning signal can be given.

BRIEF DESCRIPTION OF THE DRAWINGS

Having described the invention in general terms, a specific embodiment will be described wit reference to the drawings showing.

DETAILED DESCRIPTION OF THE PREFERRED EMBODIMENTS

Figure 1:
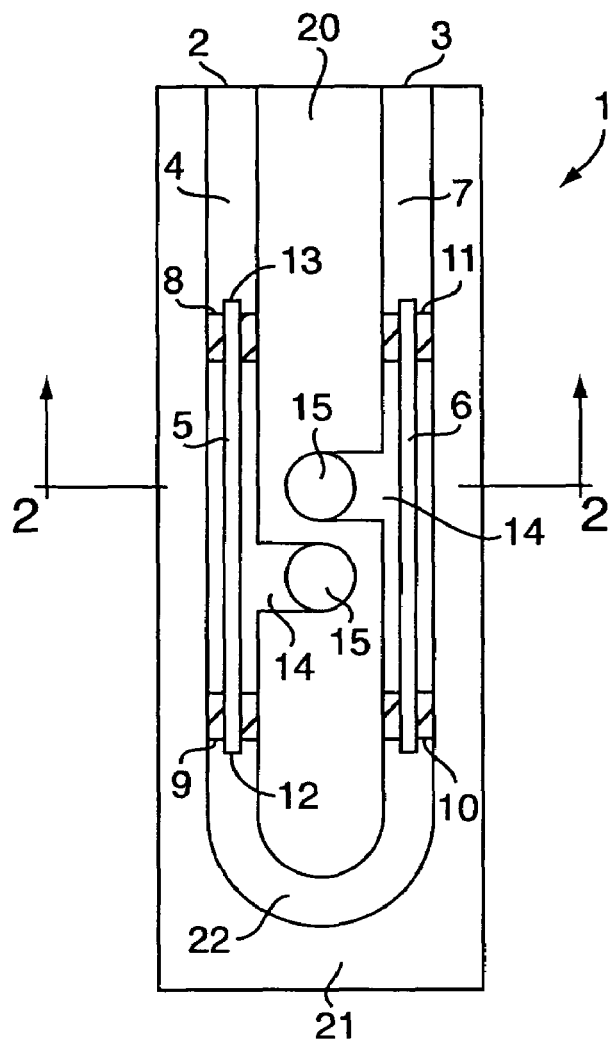
FIG. 1 is a sectional view of the carrier showing one carrier part, the seal and the capillary tubes.
Figure 2:
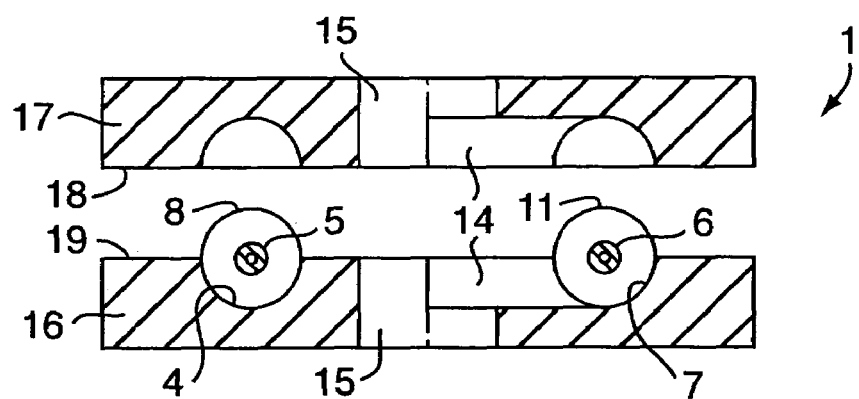
FIG. 2 is a sectional view of the carrier showing both carrier parts and the capillary tubes with seals.

As shown in FIG. 1, a part 16 of a capillary carrier 1, has an upper section 20 and a lower section 21. A channel part 4,7 and 22 has a concave profile in the part 16, and when part 16 and mirrored part 17 are put together, best seen in FIG. 2, this concave profile in the two parts will form a fluid channel through the capillary carrier.

The capillary carrier of FIG. 1 has an inlet 2 and outlet 3, whereby fluid from a fluid system can flow to and from the channel of the capillary carrier 1. A capillary tube 5 and 6 is positioned in the capillary carrier part 16 and is supported by seals 8, 9, 10 and 11. When the capillary carrier part 17 is put together with capillary carrier part 16, the seals 8, 9, 10 and 11 will seal the capillary tube 5 and 6 relative to the channel near the inlet end 13 and the outlet end 12. A fluid path through the capillary carrier is formed, running from inlet 2 through channel part 4 to inlet end 13, through capillary tube 5 to outlet end 12, through channel part 22 to inlet end of capillary tube 6, through capillary tube 6 to outlet end of capillary tube 6, and through channel part 7 to outlet 3.

Two areas 14 are formed between the seals 8 and 9, and 10 and 11. These areas 14 are in communication with a hole 15, running through both bottom 16 and top 17 part of the capillary carrier 1. Under normal conditions the areas 14 will be dry, as fluid is unable to pass the seals 8, 9, 10 and 11, and unable to escape from the capillary tube between the inlet end 13 and the outlet end 12. In case of a leak through one of the seals 8-11, or in case of a broken capillary tube, fluid will however penetrate into the area 14, and from there further on through the hole 15. A fault situation in the capillary carrier will thus have no effect on dosage amount, as fluid simply will be led away through hole 15.

The two parts 16 and 17 should be sealed against each other, besides in the area of the fluid channel. This sealing occurs through gluing the two surfaces 18 and 19, with a glue resistant against the fluid, which is to be led through the capillary carrier. It is, of course, of importance that no leak of fluid is possible from one part of the fluid channel to another, through the surface area 18 and 19.

What is claimed is:

1. A carrier with an inlet and an outlet, said carrier comprising:
   a channel formed within said carrier and extending between said inlet and said outlet;
   at least one capillary tube being arranged within said channel; and
   sealing elements, by which said capillary tube is sealingly fixed to said channel, said sealing elements being arranged at least near an inlet portion and an outlet portion of said capillary tube;
   wherein an area is defined by a part of said channel, said sealing elements and the exterior of said capillary tube, said area is in connection with the exterior of said carrier through a fluid communication path, whereby a possible fluid leak across said sealing elements will be led to this area, and from there to the exterior of said carrier;
   wherein said carrier forms an upper section and a lower section, each of said capillary tubes has said inlet portion in one of said sections and said outlet portion in the other of said sections; and
   wherein said channel is formed as at least two legs, each leg extending from said upper to said lower section, and where two neighboring legs are in fluid communication with each other in one of said upper or said lower section.

2. The carrier in accordance with claim 1, wherein two parts form said carrier, and where said channel is formed between said two parts when they are put together.

3. The carrier in accordance with claim 2, wherein said two parts are glued together, the glue in addition performing a sealing between said two parts, prevents fluid from penetrating from said channel into the surface area between said two parts.

4. The carrier in accordance with claim 2, wherein said two parts are held together by a snap-system, and where a sealing material between the two surfaces facing towards each other prevents fluid from penetrating from said channel into the surface area between said two parts.

5. The carrier in accordance with claim 1, wherein the material forming said carrier has a heat transfer capability such that temperature control of said capillary tube can be done by controlling the exterior surface temperature of said carrier.

6. The carrier in accordance with claim 1, wherein said inlet and said outlet both are placed in one of said upper or lower section.

7. The carrier in accordance with claim 1, wherein a capillary tube is arranged within each of said legs in said carrier.

8. The carrier in accordance with claim 1, wherein detection means are in connection with said area, by which a possible fluid leak across said sealing elements is detectable.

9. A capillary carrier comprising:
   a carrier body having a channel defined therein, the channel extending between an inlet and an outlet of the carrier body, the carrier body also having a first fluid communication path defined therein, the first fluid communication path extending between a first portion of the channel and an exterior of the carrier body;
   a first capillary tube arranged within the channel;
   at least two sealing elements arranged within the channel, the at least two sealing elements suspending the capillary tube within the channel such that the first portion of the channel is isolated from the inlet and the outlet by the at least two sealing elements and the capillary tube;
   a second capillary tube arranged within the channel in series with the at least one capillary tube; and
   at least another two sealing elements arranged within the channel, the other two sealing elements suspending the second capillary tube within the channel such that a second portion of the channel is isolated from the inlet and the outlet by the other two sealing elements and the second capillary tube;
   wherein the first or a second fluid communication path extends between the second portion of the channel and the exterior of the carrier body.

10. The capillary carrier of claim 9, wherein the carrier body is formed from two parts joined on opposed surfaces, each opposed surface having a recess defined therein, the recesses on the opposed surfaces being substantially aligned to form the channel therebetween.

11. The capillary carrier of claim 10, wherein a sealing material is arranged between the opposed surfaces to inhibit leakage from the channel to between the opposed surfaces.

12. The capillary carrier of claim 11, wherein the two parts are snap-fit together.

13. The capillary carrier of claim 12, wherein the sealing material is glue and the snap-fit applies a force necessary for glue curing.

14. The capillary carrier of claim 9, wherein the channel has a bend within the carrier body such that at least two legs are formed with the bend between them, the first capillary tube being arranged within one of the at least two legs and the second capillary tube being arranged within another of the at least two legs.

15. The capillary carrier of claim 14, wherein the at least two legs are substantially parallel and the bend between the legs traverses approximately 180 degrees.

16. The capillary carrier of claim 15, wherein the inlet and the outlet are arranged proximate to one another on the exterior of the carrier body.

* * * * *